US007846100B2

(12) United States Patent
Gaud et al.

(10) Patent No.: US 7,846,100 B2
(45) Date of Patent: Dec. 7, 2010

(54) MEDICAL IMAGING SYSTEM BASED ON A TARGETED CONTRAST AGENT

(75) Inventors: Emmanuel Gaud, Genève (CH); Peter Frinking, Genèva (CH); Nicolas Rognin, Genève (CH); Sibylle Pochon, Genève (CH); Nathalie Biolluz, Genève (CH); Marcel Arditi, Genèva (CH)

(73) Assignee: Bracco International BV, Amsterdam (NL)

( * ) Notice: Subject to any disclaimer, the term of this patent is extended or adjusted under 35 U.S.C. 154(b) by 569 days.

(21) Appl. No.: 11/885,723

(22) PCT Filed: Mar. 3, 2006

(86) PCT No.: PCT/EP2006/060464

§ 371 (c)(1),
(2), (4) Date: Sep. 4, 2007

(87) PCT Pub. No.: WO2006/094951

PCT Pub. Date: Sep. 14, 2006

(65) Prior Publication Data

US 2008/0139942 A1  Jun. 12, 2008

(30) Foreign Application Priority Data

Mar. 3, 2005  (EP) ................................ 05101665

(51) Int. Cl.
*A61B 8/14* (2006.01)
(52) U.S. Cl. ...................................... 600/458; 128/916
(58) Field of Classification Search .................. 600/437, 600/443, 458; 128/916
See application file for complete search history.

(56) References Cited

U.S. PATENT DOCUMENTS

2004/0059218 A1*  3/2004  Kanda et al. ................. 600/437
2007/0073146 A1*  3/2007  Phillips et al. .............. 600/437

FOREIGN PATENT DOCUMENTS

EP  0 458 745 A1  5/1991

(Continued)

OTHER PUBLICATIONS

Dayton P A et al, "Optical and acoustical dynamics of microbubble contrast agents inside neutrophils", Biophysical Journal, New Yourk, US, US, vol. 80, No. 3, Mar. 2001, pp. 1547-1556, XP002266568.

(Continued)

*Primary Examiner*—Eric F Winakur
*Assistant Examiner*—Michael T Rozanski
(74) *Attorney, Agent, or Firm*—Bryan A. Santarelli; Graybeal Jackson LLP

(57) ABSTRACT

A medical imaging system is proposed. The system includes means for providing a plurality of echo signals indicative of a response of a body part to a plurality of ultrasound pulsed waves having different acoustic pressures, the body part including a tissue being perfused with a contrast agent, and means for discriminating in the echo signals a contribution of a first type of contrast agent from a contribution of a second type of contrast agent and/or of the tissue, at least one harmonic component of the contribution of the first type of contrast agent having an acoustic power changing according to a first dependency law on the acoustic pressure and the at least one harmonic component of the contribution of the second type of contrast agent and/or of the tissue having an acoustic power changing according to at least one second dependency law on the acoustic pressure, wherein the means for discriminating includes means for significantly reducing the at least one harmonic component of the contribution of the second type of contrast agent and/or of the tissue with respect to the at least one harmonic component of the contribution of the first type of contrast agent according to the corresponding dependency laws.

23 Claims, 8 Drawing Sheets

FOREIGN PATENT DOCUMENTS

| | | |
|---|---|---|
| EP | 0 554 213 A1 | 8/1993 |
| EP | 1 228 770 A1 | 8/2002 |
| WO | WO 91/15244 | 10/1991 |
| WO | WO 94/09829 | 5/1994 |
| WO | WO 95/16467 | 6/1995 |
| WO | WO 2004/006964 A1 | 1/2004 |
| WO | 2006018433 | 2/2006 |

OTHER PUBLICATIONS

Dayton P A et al., "Ultrasonic enhancement of / spl Alph/v/spl beta/3 expressing-cells with targeted contrast agents", 2003 IEEE Ultrasonics Symposium Proceedings, Honolulu, Hawaii, Oct. 5, vol. 1 of 2, Oct. 5, 2003, pp. 540-543, XP010702713.

Bloch Susannah H et al., "Targeted imaging using ultrasound contrast agents. Progress and opportunities for clinical and research applications", IEEE Engineering in Medicine and Biology Magazine: The Quarterly Magazine of the Engineering in Medicine & Biology Society, Sep.-Oct. 2004, vol. 23, No. 5, Sep. 2004, pp. 18-29, XP002342935.

G.M. Lanza and S.A. Wickline, Targeted Ultrasonic Contrast Agents for Molecular Imaging and Terapy, Progress in Cardiovascular Diseases, 44(1), 2001, 13-31.

International Search Report for PCT/EP2006/060464 dated Jun. 23, 2006.

* cited by examiner

MEDICAL IMAGING SYSTEM BASED ON A TARGETED CONTRAST AGENT

PRIORITY CLAIM

This application claims priority from PCT/EP2006/060464, published in English, filed Mar. 3, 2006, which claims priority from European patent Application No. 05101665.7, filed Mar. 3, 2005, which are incorporated herein by reference.

TECHNICAL FIELD

The present invention relates to the medical imaging field. More specifically, the present invention relates to enhancing the different echographic response between a contrast agent and a tissue and/or between different types of contrast agent.

BACKGROUND

Medical imaging is a well-established technique in the field of equipments for medical applications. A specific medical imaging technique is based on the analysis of an echo signal that results from the application of ultrasound waves to a patient. This technique can advantageously be implemented with the administration of an ultrasound contrast agent (UCA) to the patient (for example, consisting of a suspension of phospholipid-stabilized gas-filled microvesicles); as the contrast agent acts as an efficient ultrasound reflector, it enhances the visualization of a vascular system within the body part where it is present.

A number of signal-processing methods are known in the art for the specific detection of the echo signal generated by the contrast agent, against the naturally occurring echo signal of the surrounding tissues. These methods all exploit, in some way or another, the particular, primarily nonlinear, modes in which contrast agent responds to ultrasound waves (in contrast with the primarily linear scattering by tissues).

Targeted contrast agents have also been proposed in the last years for facilitating the detection of specific pathologies. These contrast agents are formulated in such a way as to bind preferably to specific targets; for example, the desired behavior is achieved by means of a targeting ligand (incorporated in the contrast agent) that binds to a specific receptor on tumoral tissues. In this way, detection of the immobilized contrast agent allows distinguishing pathologies that would be otherwise difficult to identify.

A possible problem associated with the above-mentioned technique is that only a relatively small fraction of the total amount of administered contrast agent actually reaches its target; conversely, most of the contrast agent continues to circulate (for example, until it is filtered in the lungs, in the kidneys and/or in the liver of the patient). Therefore, the echo signal that is measured is the result of different contributions, which are due to the contrast agent immobilized on the target, to the free-flowing (circulating) contrast agent and to the surrounding tissues. However, it is quite difficult to distinguish the echo signal generated by the immobilized contrast agent from the one generated by the circulating contrast agent and the tissues. This adversely affects the spatial delineation and the quantification of the immobilized contrast agent, thereby hindering the correct detection of the pathologies of interest.

Attempts have been made to improve the discrimination of the immobilized contrast agent. For example, "P. A. Dayton, D. Pearson, J. Clark, S. Simon, P. Schumann, R. Zutshi, T. Matsunaga, K. W. Ferrara, Ultrasonic Enhancement of $\alpha_v\beta_3$ Expressing-Cells With Targeted Contrast Agents, 2003 IEEE Ultrasonics Symposium", which is incorporated by reference, proposes a solution that is based on the observation that the echo signal corresponding to the immobilized contrast agent has a narrower bandwidth with respect to the one corresponding to the circulating contrast agent (with the echo signal for the immobilized contrast agent that also has a lower mean frequency and a higher amplitude). The cited document then mentions the possibility of discriminating the different contributions in the echo signal exploiting the large bandwidth that is observed for the circulating contrast agent only (for example, using harmonic imaging strategies).

However, no solution available in the art is completely satisfactory. Therefore, a need is perceived for a technique that would allow detecting the immobilized contrast agent with an acceptable degree of accuracy. Particularly, the problem of efficiently discriminating the immobilized contrast agent from the circulating contrast agent and from the tissues is still unresolved. All of the above hinders the clinical application of the medical imaging techniques based on the targeted contrast agents.

Furthermore, in some instances, it may be desirable to have alternative methods (i.e., different from those known in the art) to distinguish a contrast agent from the surrounding tissues and/or from another (different) contrast agent.

SUMMARY

In its general terms, an embodiment of the present invention is based on the recognition of a specific harmonic response of certain types of contrast agents, which allows their discrimination against the tissues and/or other contrast agents.

More specifically, an embodiment of the invention proposes a medical imaging system. The system includes means for providing a plurality of echo signals; the echo signals are indicative of a response of a body part to a plurality of ultrasound pulsed waves, which have (two or more) different acoustic pressures. The body part includes a tissue being perfused with a contrast agent. Means is also provided for discriminating (in the echo signals) a contribution of a first type of contrast agent from a contribution of a second (different) type of contrast agent and/or of the tissue. A harmonic component (one or more) of the contribution of the first type of contrast agent has an acoustic power, which changes according to a first dependency law on the acoustic pressure (such as in a linear way); conversely, the same harmonic component of the contribution of the second type of contrast agent and/or of the tissue has an acoustic power, which changes according to a second dependency law (or more) on the acoustic pressure (such as in a quadratic way). The means for discriminating includes means for significantly reducing the harmonic component of the contribution of the second type of contrast agent and/or of the tissue, with respect to the harmonic component of the contribution of the first type of contrast agent, according to the corresponding dependency laws.

In an embodiment of the invention, the proposed solution is applicable to the detection of the immobilized contrast agent with respect to the circulating contrast agent and/or the tissue.

Alternatively, the same solution is applicable to the detection of the contrast agent with respect to the tissue; in this case, the contrast agent is in the form of microvesicles, with the corresponding dependency law that has a power lower 32 dB/decade.

Typically, those microvesicles are deflated gas-filled microvesicles.

For example, it is possible to use phospholipid-stabilized gas-filled microvesicles with low concentration of a gas having relatively low solubility in water and/or high molecular weight.

In an embodiment of the invention, the first dependency law (e.g., for the immobilized contrast agent or for the deflated gas-filled microvesicles) is a substantial linear dependency law, while the second dependency law (e.g., for the circulating contrast agent and for the tissue or for the sole tissue, respectively) is a substantial quadratic dependency law.

More specifically, the substantial linear dependency law has a power from about 16 dB/decade to about 24 dB/decade, and the substantial quadratic dependency law has a power from about 32 dB/decade to about 48 dB/decade.

An embodiment of the invention is based on the analysis of the second harmonic component of the echo signals.

A suggested implementation of an embodiment of the solution of the invention involves the combination of the echo signals, so as to substantially remove the harmonic component changing with the quadratic dependency law.

Moreover, a fundamental component of each echo signal and/or of the combined echo signals is filtered out.

Particularly, the desired result can be achieved by means of two echo signals (a first one corresponding to a first acoustic pressure, and a second one corresponding to a second acoustic pressure that is equal to the first acoustic pressure multiplied by a predetermined factor); in this case, a difference between the first echo signal multiplied by the square of such factor and the second echo signal is calculated.

In an embodiment of the invention, said factor is comprised between 1.5 and 4.

As another enhancement, the acoustic pressures of the ultrasound pulsed waves are lower than a threshold value that causes a destruction of substantially 10% of the contrast agent in the body part.

In a specific application, the contrast agent includes phospholipid-stabilized gas-filled microvesicles; in this case, the acoustic pressures are comprised between 20 kPa and 500 kPa.

A way to further improve the solution is to apply the algorithm on an envelope of (radio-frequency) echo signals.

In a particular embodiment of the invention, the system also includes means for applying the ultrasound pulsed waves to the body part and means for acquiring the corresponding echo signals (for example, an imaging probe).

Another embodiment of the present invention proposes a corresponding medical imaging method.

A further embodiment of the present invention proposes a computer program for performing the method.

A still further embodiment of the invention proposes a product embodying the computer program.

Another embodiment of the present invention proposes the use of a contrast agent including the above-described microvesicles in this medical imaging method.

A further embodiment of the present invention proposes the use of the same microvesicles for the preparation of a contrast agent to be used in the medical imaging method.

BRIEF DESCRIPTION OF THE DRAWINGS

Features and advantages of one or more embodiments of the invention will be best understood by reference to the following detailed description, given purely by way of a non-restrictive indication, to be read in conjunction with the accompanying drawings.

DETAILED DESCRIPTION

Figure 1:
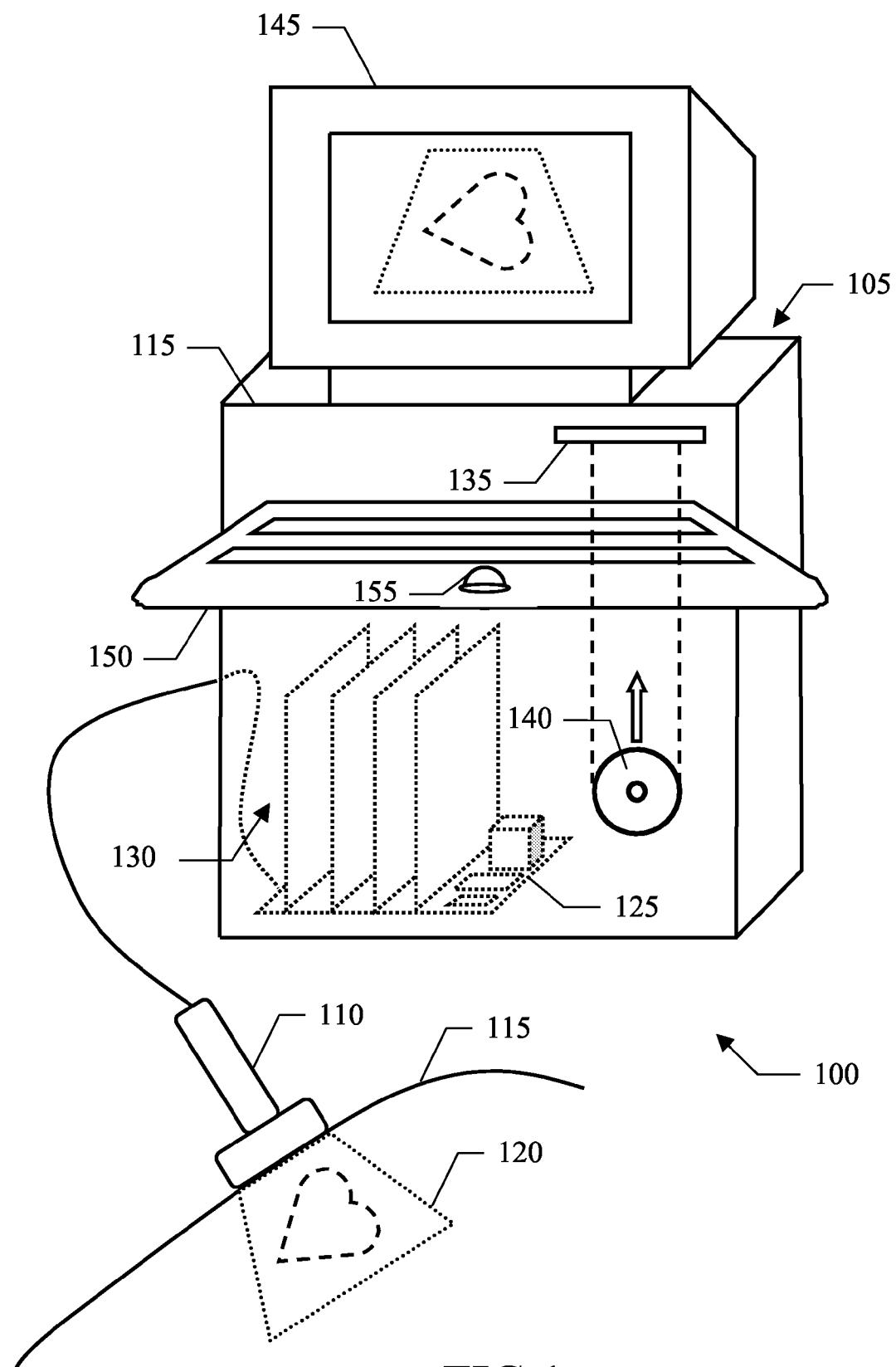
FIG. 1 is a pictorial representation of a medical imaging system in which a solution according to an embodiment of the invention is applicable.

With reference in particular to FIG. 1, a medical imaging system 100 is illustrated. Particularly, the system 100 includes an ultrasound scanner having a central unit 105 with a (hand-held) transmit-receive imaging probe 110 (for example, of the linear-, convex-, phased-, or matrix-array type). The imaging probe 110 transmits ultrasound waves consisting of a sequence of pulses (for example, having a center frequency between 2 and 10 MHz), and receives echo signals resulting from the backscattering of the ultrasound waves; for this purpose, the imaging probe 110 is provided with a transmit/receive multiplexer, which allows using the imaging probe 110 in the above-mentioned pulse-echo mode.

In operation, the imaging probe 110 is typically placed in contact with the skin of a patient 115 in the area of a body part 120 to be analyzed; the body part 120 has been previously perfused with a contrast agent, which can be administered to the patient 115 either with a continuous flow (by means of a suitable pump) or as a bolus (typically by hand with a syringe).

Suitable contrast agents include suspensions of gas bubbles in a liquid carrier; typically, the gas bubbles have diameters on the order of 0.1-5 μm, so as to allow them to pass through the capillary bed of the patient. The gas bubbles are generally stabilized by entraining or encapsulating the gas or a precursor thereof into a variety of systems, including emulsifiers, oils, thickeners, sugars, proteins or polymers; stabilized gas bubbles are referred to as gas-filled microvesicles. The microvesicles include gas bubbles dispersed in an aqueous medium and bound at the gas/liquid interface by a very thin envelope involving a surfactant, i.e., an amphiphilic material (also known in this case as microbubbles). Alternatively, the microvesicles include suspensions in which the gas bubbles are surrounded by a solid material envelope formed of lipids or of natural/synthetic polymers (also known as microballoons or microcapsules). Another kind of contrast agent includes suspensions of porous microparticles of polymers or other solids, which carry gas bubbles entrapped within the pores of the microparticles. Examples of suitable aqueous suspensions of microvesicles, in particular microbubbles and microballoons, and of the preparation thereof are described in EP-A-0458745, WO-A-91/15244, EP-A-0554213, WO-A-94/09829 and WO-A-95/16467 (the entire disclosures of which are herein incorporated by reference). A commercial ultrasound contrast agent comprising gas-filled microvesicles is SonoVue® by Bracco International BV.

The contrast agent is substantially free to circulate within the body of the patient, so as to be received by the body part under analysis; for example, the contrast agent can move along the gastrointestinal tract (in case of oral administration), or within the vascular system (in case of intravascular administration). However, in an embodiment of the invention the contrast agent is also capable of being immobilized on a selected (biological) target, so as to remain in a substantially fixed position for the whole duration of the analysis process (or at least a large extent thereof).

For this purpose, the contrast agent may be formulated in such a way as to selectively bind to the desired target by means of a specific interaction therewith; in this case, it is commonly referred to as targeted contrast agent. For example, this behavior can be achieved by incorporating a targeting ligand capable of selectively binding (such as through biochemical affinity and/or electrostatic interaction) to a desired tissue or receptor. Examples of targeting ligands (which may be inserted into a membrane of the microbubbles) are monoclonal antibodies, peptides, or polysaccharides. The term tissue includes within its meaning individual cells as well as aggregates of cells, such as membranes or organs. The term refers to either normal (healthy) or abnormal (pathological) cells or aggregates of cells. Examples of tissues are myocardial tissues (including myocardial cells and cardiomyocites), membranous tissues (such as endothelium and epithelium), and connective tissues; examples of pathological tissues are infarcted heart tissues, blood clots, atherosclerotic plaques and tumoral tissues. The receptors include any molecular structure located on the tissues (for example, within the cells or on their surfaces), which is capable to selectively bind to a specific substance. Exemplary receptors are glycoprotein GPIIbIIIa or fibrin (for example, located in blood clots or thrombi) or KDR (for example, located in tumoral tissues). Examples of suitable targeted contrast agents and of targeting ligands are described in "G. M. Lanza and S. A. Wickline, Targeted Ultrasonic Contrast Agents for Molecular Imaging and Therapy, Progress in Cardiovascular Diseases, 44(1), 2001, 13-31", and in the co-pending International Patent Application No. PCT/EP2005/054041 filed on 17 Aug. 2005 (the entire disclosures of which are herein incorporated by reference).

Also contrast agents without specific targeting ligands may nevertheless be immobilized on specific locations of the patients by means of non-specific interactions therewith. For example, depending on their formulation and size, certain gas-filled microvesicles may be rapidly recognized as non-self components of the blood, thus being opsonized by blood proteins and then phagocytosed by monocytes or macrophages. In this case, generally, a large fraction of the gas-filled microvesicles ends up in the liver. Alternatively, gas-filled microvesicles (which are less rapidly recognized as non-self components of the blood) may extend their circulation time up to at least 20 minutes. For these gas-filled microvesicles a slow accumulation thereof can occur in certain organs (for example, the kidney); therefore, at late times after administration, the gas-filled microvesicles can be slowly moving or completely stopped in these organs.

As it will be understood by those skilled in the art, when the contrast agent (either with or without a targeting ligand) is not immobilized on a specific target or location, it is otherwise substantially free to circulate (depending on the particular way of administration) within the body of the patient.

In a different embodiment of the invention, the contrast agent comprises deflated gas-filled microvesicles.

In the present description and claims, the term "deflated gas-filled microvesicles" refers to gas-filled microvesicles, which have partially lost their initial content of gas or, more in general, which have a content of gas lower than the content of the microvesicles after they have been prepared as an aqueous suspension at atmospheric pressure. These kind of microvesicles can be obtained, for instance, by using microvesicles filled with a mixture of gases, one with relatively low solubility in water and the other with relatively high solubility in water, including, for instance, those disclosed in WO-A-95/16467, which is incorporated by reference. These "mixed-gas" microvesicles may comprise from 0.5% to 30% by volume, for example, from 3% to 20%, or from 5% to 15% of a gas having low solubility in water, for example, lower than 0.0283 ml of gas per ml of water; for example, said gas also has a relatively high molecular weight, for example, higher than 80 daltons (Da). The remainder of the internal volume of the microvesicles is another gas with either higher solubility in water and/or lower molecular weight. For example, the low-solubility gas is a fluorine-containing biocompatible gas, such as sulphur hexahexafluoride or perfluoro hydrocarbons, including $SF_6$, $CF_4$, $C_2F_6$, $C_3F_8$, $C_4F_8$, $C_4F_{10}$, $C_5F_{10}$, $C_5F_{12}$ or $C_6F_{12}$, for example, being $SF_6$, $C_3F_8$ or $C_4F_{10}$, or $C_4F_{10}$. The other gas can be any gas with higher solubility in water (e.g., higher than 0.01 ml of gas per ml of water) and/or with lower molecular weight; for example, this gas includes air, nitrogen, carbon dioxide or mixtures thereof. The gas mixture is entrapped in a stabilizing layer comprising a phospholipid. Examples of suitable phospholipids include esters of glycerol with one or two (equal or different) residues of fatty acids and with phosphoric acid, wherein the phosphoric acid residue is in turn bound to a hydrophilic group, such as choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or may be completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. For example, saturated fatty acids such as myristic acid, palmitic acid, stearic acid and arachidic acid are employed. Further examples of phospholipid are phosphatidic acids, i.e., the diesters of glycerol-phosphoric acid with fatty acids; sphingolipids such as sphingomyelins, i.e., those phosphatidylcholine analogs where the residue of glycerol diester with fatty acids is replaced by a ceramide chain; cardiolipins, i.e., the esters of 1,3-diphosphatidylglycerol with a fatty acid; glycolipids such as gangliosides GM1 (or GM2) or cerebrosides; glucolipids; sulfatides and glycosphingolipids. As used herein, the term phospholipids include either naturally occurring, semisynthetic or synthetically prepared products that can be employed either singularly or as mixtures. Examples of naturally occurring phospholipids are natural lecithins (phosphatidylcholine (PC) derivatives) such as, typically, soya bean or egg yolk lecithins. Examples of semisynthetic phospholipids are the partially or fully hydrogenated derivatives of the naturally occurring lecithins. Suitable phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or sphingomyelin. Suitable phospholipids further include modified phospholipids, e.g., phospholipids where the hydrophilic group is in turn bound to another hydrophilic group. Examples of modified phospholipids are phosphatidylethanolamines modified with polyethylenglycol (PEG), i.e., phosphatidylethanolamines where the hydrophilic ethanolamine moiety is linked to a PEG molecule of variable molecular weight (e.g., from 300 to 5000 daltons), such as DPPE-PEG (or DSPE-, DMPE- or DAPE-PEG), i.e., DPPE (or DSPE, DMPE, or DAPE) having a PEG polymer attached thereto. Other excipients or additives may be either present in the dry formulation of the microbubbles or added together with the aqueous carrier used for the reconstitution thereof, without necessarily being involved (or only partially involved) in the formation of the stabilizing envelope of the microbubbles. These include pH regulators, osmolality adjusters, viscosity enhancers, emulsifiers, bulking agents, and so on (used in conventional amounts). For instance, compounds like polyoxypropylene glycol and polyoxyethylene glycol as well as copolymers thereof can be used. Examples of viscosity enhancers or stabilizers are compounds selected from linear and cross-linked poly- and oligo-saccharides, sugars, and hydrophilic polymers like polyethylene glycol.

As the preparation of gas-filled microbubbles may involve a freeze drying or spray drying step, it may be advantageous to include a lyophilization additive in the formulation, such as an agent with cryoprotective and/or lyoprotective effect and/or a bulking agent, for example, an amino-acid such as glycine, a carbohydrate, e.g., a sugar such as sucrose, mannitol, maltose, trehalose, glucose, lactose or a cyclodextrin, or a polysaccharide such as dextran, or a polyglycol such as polyethylene glycol.

The microvesicles may be produced according to any method known in the art. Typically, the manufacturing method involves the preparation of a dried powdered material comprising an amphiphilic material as above indicated, for example by lyophilization (freeze drying) of an aqueous or organic suspension comprising said material.

Without willing to be bound to any particular theory, it is believed that these microvesicles filled with a mixture of gas will tend to release a certain amount of the more soluble gas in the aqueous medium where they are typically dispersed in. This is for instance the case when the gas-filled microvesicles are administered into the vascular system, where also the blood pressure can play a role in the release of the more soluble gas. This partial release of the more soluble gas will result in a corresponding partial deflation of the microvesicles, which is responsible for the particular behavior observed. The release of the high-solubility gas may vary depending on the type of gas composing the mixture and on the relative amounts thereof. For instance, when mixtures of $C_4F_{10}$ and nitrogen are taken into consideration, when the amount of $C_4F_{10}$ is lower than about 30% by volume, a relative fast release of sufficient amount of nitrogen takes place already after few minutes from the formation of the suspension, thus allowing a sufficient deflation of the microvesicles.

Furthermore, deflated gas-filled microvesicles can also be obtained by using a filling gas, which is only partially soluble in water (e.g., with a solubility between 0.01 and 0.001 ml of gas per ml of water). Again, the partial dissolution in time of a certain amount of the gas in the aqueous medium will determine the desired partial deflation of the microvesicles.

In addition, deflated gas-filled microvesicles may also be obtained by reconstituting (with an aqueous solution) a lyophilized residue in a vial containing a gas at a pressure lower than the atmospheric one, as disclosed for instance in the European Patent EP1228770, which is incorporated by reference. Once in the presence of the atmospheric pressure, the lower pressure inside the microvesicles will then determine a corresponding partial deflation thereof.

Finally, deflated gas-filled microvesicles can also be obtained by mechanical treatments of gas-filled microvesicles, as disclosed for instance in the International Patent Application WO2004/006964, which is incorporated by reference.

If desired, any of the above-defined gas-filled microvesicles may also be formulated with any suitable targeting ligand as previously described.

Referring back to the figure, the central unit 105 houses a motherboard 125, on which the electronic circuits controlling operation of the scanner 100 (such as a microprocessor, a working memory and a hard-disk drive) are mounted. Moreover, one or more daughter boards (denoted as a whole with 130) are plugged on the motherboard 125; the daughter boards 130 provide the electronic circuits for driving the imaging probe 110. The scanner 100 may also be equipped with a drive 135 for reading removable disks 140 (such as floppy-disks). A monitor 145 is used to display images representing the body part 120 under analysis. Operation of the system 100 is controlled by means of a keyboard 150, which is connected to the central unit 105 in a conventional manner; for example, the keyboard is provided with a trackball 155 that is used to manipulate the position of a pointer (not shown in the figure) on a screen of the monitor 145.

When a contrast agent capable of being immobilized on a selected target/location is administered to the patient 115, the echo signals that are measured in-vivo result from the superimposition of different contributions, typically generated by the immobilized contrast agent, the circulating contrast agent, and the surrounding tissues. A property of the echo signals has been identified that is specific for the immobilized contrast agent (with respect to the circulating contrast agent and to the tissues). This peculiar property includes a different harmonic response of the immobilized contrast agent as compared to the ones of the circulating contrast agent and of the tissues. The property defines a corresponding signature of the immobilized contrast agent, which may then be used to discriminate the contribution of the immobilized contrast agent in the echo signals as distinct from those of the circulating contrast agent and of the tissues.

Figure 2B:
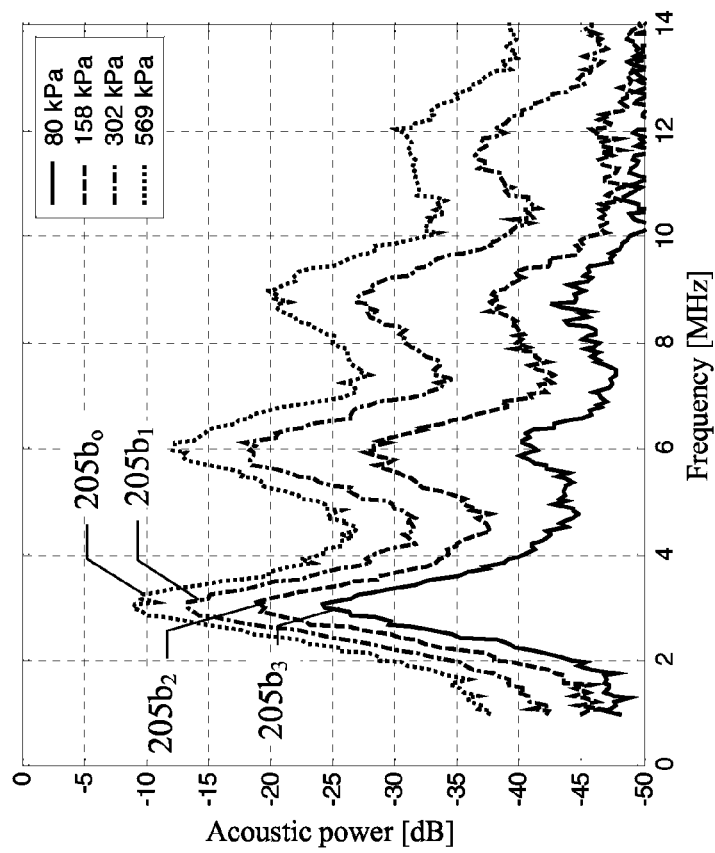
FIGS. 2a and 2b show exemplary frequency spectra of an echo signal relating to an immobilized contrast agent and to a circulating contrast agent, respectively, at different acoustic pressures of corresponding ultrasound waves.
Figure 2A:
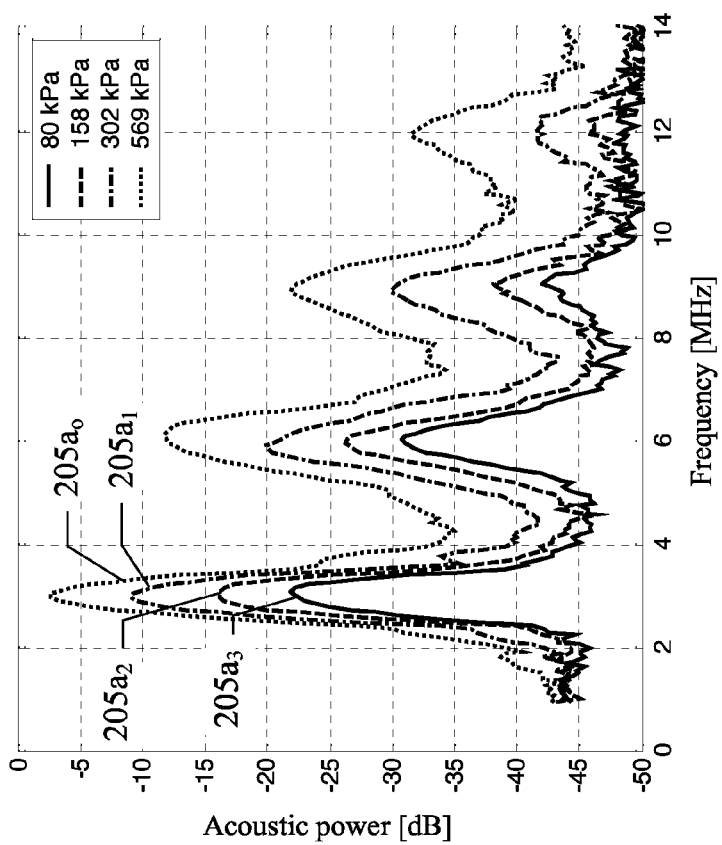

Considering in particular FIGS. 2a and 2b, a different dependency of the harmonic components of the echo signals on an acoustic pressure of the corresponding ultrasound waves is illustrated. These results were obtained by means of experimental observations, which were performed in-vitro at different acoustic pressures according to the methodology described in the subsequent examples. The term "acoustic pressure" as utilized herein refers to the "peak negative pressure" of the transmitted ultrasound pulsed wave, which is typically determined by a corresponding amplitude of a voltage waveform exciting the imaging probe. Thus, ultrasound pulsed waves with different acoustic pressures are characterized by different peak negative pressures, obtainable by exciting the imaging probe with corresponding amplitudes of the voltage waveform. In other words, the ultrasound waves with different acoustic pressures will have different values of acoustic power at their fundamental frequency.

More in detail, FIG. 2a shows several exemplary frequency spectra $205a_0$-$205a_3$ of the echo signals relating to the immobilized contrast agent (in the form of gas-filled microvesicles) alone. The frequency spectra $205a_0$-$205a_3$ plot an acoustic power of the echo signal (relative to the one of the corresponding ultrasound waves) against the frequency. The frequency spectra $205a_0$-$205a_3$ have been measured in response to ultrasound waves (having a center frequency of 3 MHz) with different acoustic pressures on the microvesicles; in the example at issue, the curves $205a_0$, $205a_1$, $205a_2$ and $205a_3$ relate to an acoustic pressure of 80 kPa, 158 kPa, 302 kPa and 569 kPa, respectively. Likewise, FIG. 2b shows corresponding exemplary frequency spectra $205b_0$-$205b_3$ of the echo signals relating to the circulating contrast agent alone (for the same acoustic pressures of the ultrasound waves). For example, the acoustic pressure can be determined by means of a hydrophone.

In both cases, the frequency spectra $205a_0$-$205a_3$ (FIG. 2a) and $205b_0$-$205b_3$ (FIG. 2b) have a fundamental component at around 3 MHz. The frequency spectra $205a_0$-$205a_3$ and $205b_0$-$205b_3$ also have a second harmonic component at around 6 MHz, and further harmonic components of higher order at increasing frequencies. As can be seen in the figures, the variation of the acoustic power of the harmonic components (and especially of the second harmonic component) as a function of the acoustic pressure significantly differs between the immobilized contrast agent and the circulating contrast agent.

Figure 3B:
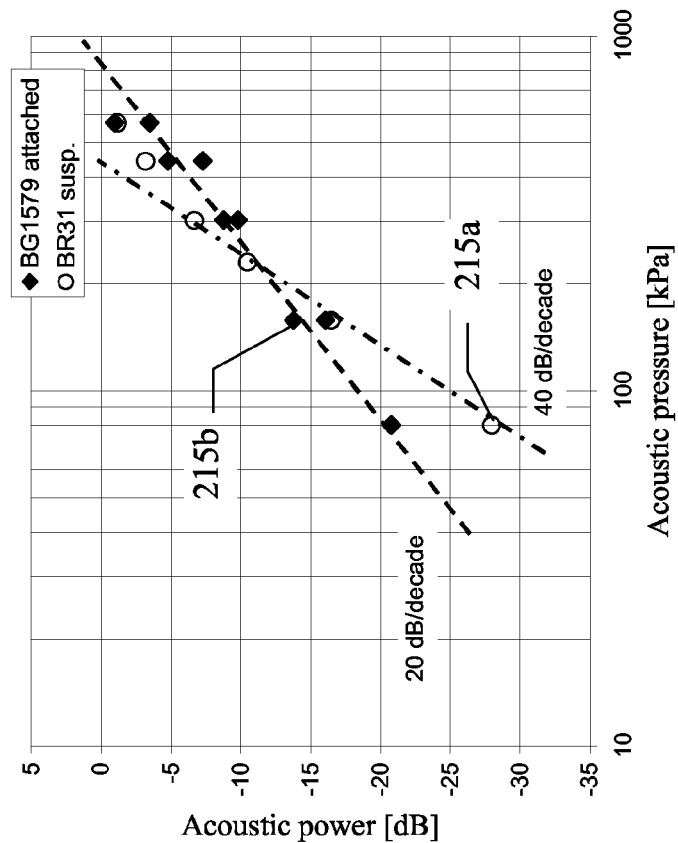
FIG. 3b shows the corresponding exemplary dependency laws (of the acoustic power of a second harmonic component of the echo signals versus the acoustic pressure of the ultrasound waves) for the immobilized contrast agent and for the circulating contrast agent, respectively.
Figure 3A:
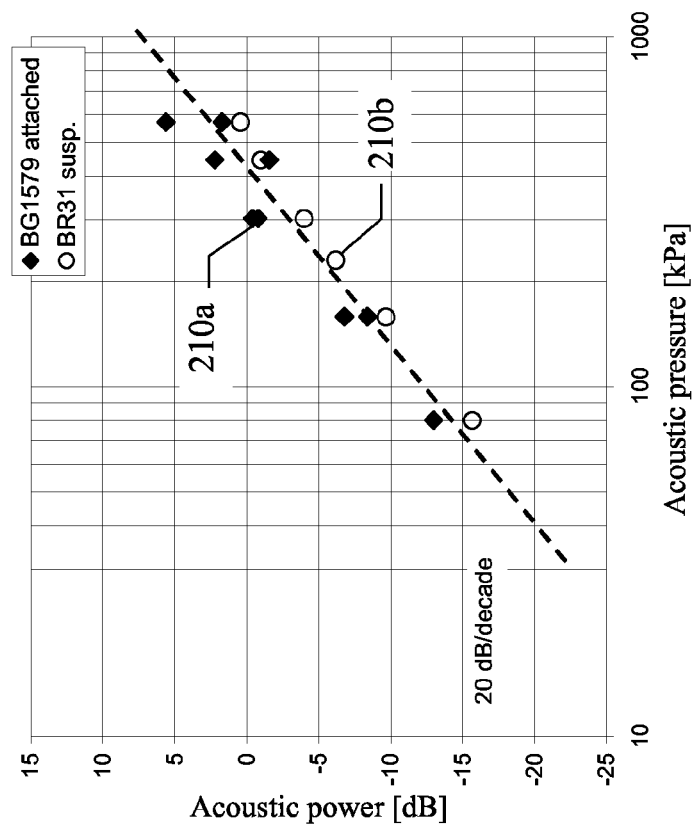
FIG. 3a shows the corresponding exemplary dependency laws (of the acoustic power of a fundamental component of the echo signals versus the acoustic pressure of the ultrasound waves) for the immobilized contrast agent and for the circulating contrast agent, respectively.

A different representation of the above-described phenomenon is illustrated in FIGS. 3a and 3b. Particularly, FIG. 3a shows the corresponding exemplary dependences of the fundamental components of the above-described frequency spectra on the acoustic pressure. More in detail, the figure plots a resulting relative acoustic power around a peak of the fundamental components of the frequency spectra (determined in a frequency band of +/−12.5% around the center frequency of 3 MHz) against the acoustic pressure (in logarithmic scale); the resulting points are denoted with 210a for the frequency spectra relating to the immobilized contrast agent and with 210b for the frequency spectra relating to the circulating contrast agent. As can be seen, the corresponding dependency laws have a slope that is equal to about 20 dB/decade in both cases; this is in agreement with a linear dependency law of the acoustic power of the echo signals on the acoustic pressure of the corresponding ultrasound waves. A similar dependency law on the acoustic pressure is also exhibited by the fundamental component corresponding to the tissues.

Likewise, FIG. 3b plots the acoustic power of the second harmonic components of the frequency spectra (determined in a frequency band of +/−12.5% around the center frequency of 6 MHz) against the acoustic pressure for the immobilized contrast agent (denoted with 215a) and for the circulating contrast agent (denoted with 215b). In this case, the corresponding dependency law for the circulating contrast agent has a slope that is equal to about 40 dB/decade; this confirms a quadratic dependency law of the acoustic power of the echo signals on the acoustic pressure, which is predicted by theory and widely documented in the scientific literature. A similar dependency law on the acoustic pressure is also exhibited by the second harmonic component corresponding to the tissues.

However, a totally unexpected result is that the corresponding dependency law for the immobilized contrast agent has a slope that is equal to about 20 dB/decade; this involves a linear dependency law of the acoustic power of the echo signals on the acoustic pressure, which is completely in contrast with the results from physical models that have been proposed for describing the oscillation behavior of standard microbubbles.

In the present description and claims, the term "linear" (when referred to the dependency law of the acoustic power of the echo signals on the acoustic pressure of the ultrasound waves) refers to those instances where the variation of the measured acoustic power is in substantially linear proportion with respect to the applied acoustic pressure, for example, with a dependency law having a power from about 16 dB/decade to about 24 dB/decade, or from about 16 dB/decade to about 22 dB/decade, such as about 20 dB/decade (i.e., 1) as described above. Similarly the term "quadratic" refers to those instances where the variation of the measured acoustic power is in substantially quadratic proportion with respect to the applied acoustic pressure, for example, with a dependency law having a power from about 32 dB/decade to about 48 dB/decade, or from about 36 dB/decade to about 44 dB/decade, such as about 40 dB/decade (i.e., 2) as described above.

In practice, this difference may be exploited to detect the immobilized contrast agent with several algorithms. For example, a possible method will be described with reference to the following table:

| | Immobilized contrast agent | | Circulating contrast agent | | Tissues | |
|---|---|---|---|---|---|---|
| | Fundamental | Harmonic | Fundamental | Harmonic | Fundamental | Harmonic |
| E1 | Fi1 | Hi1 | Fc1 | Hc1 | Ft1 | Ht1 |
| E2 = k∃E1 | Fi2 = k∃Fi1 | Hi2 = k∃Hi1 | Fc2 = k∃Fc1 | Hc2 = k²∃Hc1 | Ft2 = k∃Ft1 | Ht2 = k²∃Ht1 |
| PE = k²∃E1 − E2 | k²∃Fi1 − Fi2 = k²∃Fi1 − k∃Fi1 = (k² − k)∃Fi1 | k²∃Hi1 − Hi2 = k²∃Hi1 − k∃Hi1 = (k² − k)∃Hi1 | k²∃Fc1 − Fc2 = k²∃Fc1 − k∃Fc1 = (k² − k)∃Fc1 | k²∃Hc1 − Hc2 = k²∃Hc1 − k²∃Hc1 = 0 | k²∃Ft1 − Ft2 = k²∃Ft1 − k∃Ft1 = (k² − k)∃Ft1 | k²∃Ht1 − Ht2 = k²∃Ht1 − k²∃Ht1 = 0 |

Particularly, E1 designates a first echo signal, which has been measured in response to ultrasound waves having a predetermined acoustic pressure P1 on the contrast agent; likewise, E2 designates a second echo signal, which has been measured in response to ultrasound waves having an acoustic pressure P2 on the contrast agent. The acoustic pressure P2 is greater than the acoustic pressure P1 by an arbitrary factor k (different from 1). For example, this result can be achieved by alternatively applying ultrasound waves with the two acoustic pressures P1,P2 and recording the corresponding echo signals E1,E2; assuming that no substantial movement has taken place in the body part between each pair of corresponding pulses of the two ultrasound waves, the recorded echo signals E1,E2 can be deemed indicative of the response of the same portions of the body part under analysis to the different ultrasound waves.

The selection of the acoustic pressures P1 and P2 is a trade-off between the opposed requirements of measuring significant echo signals (i.e., high acoustic pressures) and of limiting the destruction of the contrast agent (i.e., low acoustic pressures). Particularly, the acoustic pressure P1 allows obtaining an acceptable level of the acoustic energy for the second (or higher) harmonic component of the echo signal E1; at the same time, the acoustic pressure P2 is lower than a threshold value causing a substantial destruction of the contrast agent in the body part. For example, the acoustic pressure P2 does not exceed the threshold value that determines a destruction of about 20% (by volume), for example of about 15%, or of about 10% of the contrast agent. The actual values of the acoustic pressures P1 and P2 typically depend on the chemical composition of the contrast agent; for instance, for phospholipid-stabilized gas-filled microbubbles the acoustic pressure P1 may be higher than about 20 KPa, or higher than about 50 KPa, while the acoustic pressure P2 may be lower than about 500 KPa, or lower than about 200 KPa. Within the above-described range, the difference between the acoustic pressures P1 and P2 is sufficient to allow differentiating the corresponding echo signals E1 and E2. In practice, this result is achieved by selecting a corresponding suitable Mechanical Index (MI) on the medical imaging system that allows a satisfactory imaging of the body part without excessive destruction of the contrast agent. For example, the ratio between the two acoustic pressures (P2/P1), defined by the factor k, may be selected to be at least 1.5, for example about 2.0, up to about 4.0 (for example, P1=60 kPa and P2=120 kPa).

Referring back to the table, Fi1 and Hi1 denote the acoustic power of the fundamental component and of the second harmonic component, respectively, for the contribution of the immobilized contrast agent (in the echo signal E1), Fc1 and Hc1 denote the acoustic power of the fundamental component and of the second harmonic component, respectively, for the contribution of the circulating contrast agent, and Ft1 and Ht1 denote the acoustic power of the fundamental component and of the second harmonic component, respectively, for the contribution of the surrounding tissues. Likewise, we denote with Fi2 and Hi2, Fc2 and Hc2, and Ft2 and Ht2 the acoustic power (of the fundamental component and of the second harmonic component) for the same contributions in the echo signal E2. Considering that the acoustic power of the second harmonic component for the immobilized contrast agent and the acoustic power of the fundamental components (in every case) change according to a linear dependency law on the acoustic pressure of the ultrasound waves, whereas the acoustic power of the second harmonic component for the circulating contrast agent and for the tissues change according to a quadratic dependency law on the acoustic pressure of the ultrasound waves, we have that the values Fi2, Hi2, Fc2 and Ft2 are equal to the corresponding values for the echo signal E1 multiplied by the selected factor k, while the values Hc2 and Ht2 are equal to the corresponding values for the echo signal E1 multiplied by the square of the selected factor k ($2^2=4$ in the example at issue).

In the same table, PE designates a processed echo signal that is calculated by subtracting the echo signal E2 from the product of the echo signal E1 by a value equal to the square of the selected factor k:

$$PE = k^2 \exists E1 - E2$$

As can be seen, this combination cancels the second harmonic components for both the circulating contrast agent and the tissues. The fundamental components of the processed echo signal PE (for the circulating contrast agent, the immobilized contrast and the tissues) may then be removed by conventional filtering techniques; the operation may be performed either before or after the above-described combination, that is on the echo signals E1,E2 or on the processed echo signal PE, respectively. The resulting second harmonic component of the processed echo signal (denoted with PH) then will contain the contribution due to the immobilized contrast agent only, that is:

$$PH = (k^2 - k) \exists Hi1.$$

This proposed solution facilitates the detection of the immobilized contrast agent; particularly, this allows discriminating the immobilized contrast agent from the circulating contrast agent, from the surrounding tissues, or from both of them. Therefore, the accuracy of any subsequent analysis of the results obtained is strongly increased.

More specifically, the increased sensitivity to the immobilized contrast agent (with respect to the circulating contrast agent and/or to the tissues) makes it possible to spatially delineate and/or quantify the immobilized contrast agent with a relatively high degree of precision; for example, this facilitates the correct diagnosis of several pathologies that would be otherwise difficult to detect.

All of the above fosters the clinical application of the imaging techniques based on the targeted contrast agents.

Figure 4A:
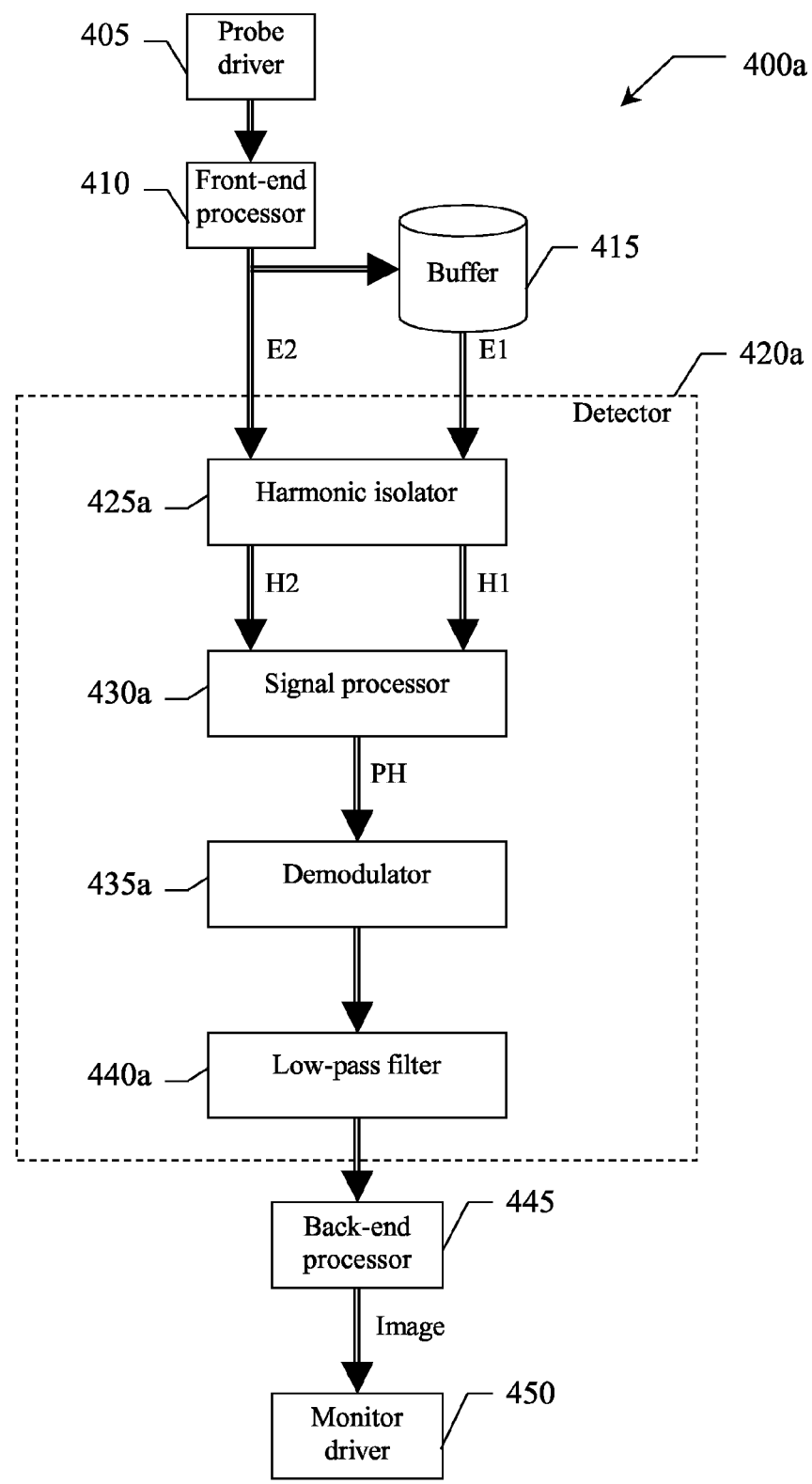
FIGS. 4a-4c depict the main software and hardware components that can be used for practicing the solution according to different embodiments of the invention.

Moving now to FIG. 4a, the main software and hardware components that can be used for practicing the solution according to an embodiment of the invention are denoted as a whole with the reference 400a. The information (programs and data) is typically stored on the hard disk and loaded (at least partially) into the working memory when the programs are running, together with an operating system and other application programs (not shown in the figure). For example, the programs can be initially installed onto the hard disk from CD-ROMs.

Particularly, a module 405 is used to drive the imaging probe (not shown), which transmits ultrasound pulsed waves to a body part and receives a corresponding radio-frequency (or RF) echo signal from said body part (previously perfused with the targeted contrast agent). For example, the imaging probe driver 405 includes a transmit beam former and pulsers for generating the ultrasound pulsed waves; in the example at issue, the imaging probe driver 405 alternatively applies pulses on each transmission direction with a first transmit voltage (V1), corresponding to the acoustic pressure P1, and with a second transmit voltage (V2), corresponding to the acoustic power P2, respectively. In practice, the parameter k thus corresponds to the voltage ratio V2/V1. The received RF echo signals are supplied to a receive front-end processor 410. The front-end processor 410 pre-amplifies the RF echo signals and applies a preliminary time-gain compensation (TGC). Typically, the (analog) RF echo signals are then converted into digital values by an Analog-to-Digital Converter (ADC), and combined into focused RF echo signals through a receive beam former.

Every line of the (raw) RF echo signals so obtained is temporarily stored into an RF line buffer 415. The current line of the RF echo signal (from the front-end processor 410) and the previous line of the RF echo signal (from the buffer 415) are both input to a detector 420a, which is designed to implement the proposed algorithm for discriminating the contribution of the immobilized contrast agent (substantially removing the ones of the circulating contrast agent and of the surrounding tissues).

Particularly, a harmonic isolator 425a receives the above-described RF echo signals (for example, corresponding to the echo signal E2 from the front-end processor 410 and to the echo signal E1 from the buffer 415). The harmonic isolator 425a extracts the second-harmonic components of both the echo signals E1 and E2. For example, this result is achieved by means of a high-pass filter, having a lower cutoff frequency comprised between the frequency of the fundamental components and the frequency of the second harmonic components (for example, between 3 MHz and 6 MHz in the example at issue, such as 4.5 MHz); alternatively, the fundamental and harmonic components of the echo signals may be separated by well-known time-frequency analyses, such as the Wigner-Ville analysis. The second harmonic component of the echo signal E1 (denoted with H1=Hi1+Hc1+Ht1) and the second harmonic component of the echo signal E2 (denoted with H2=Hi2+Hc2+Ht2) are passed to a signal processor 430a. The signal processor 430a amplifies and subtracts the harmonic echo signals H1 and H2 according to the above-described algorithm, so as to obtain the harmonic processed echo signal PH (only including the contribution due to the immobilized contrast agent):

$$PH = k^2 \exists H1 - H2 = k^2 \exists Hi1 + k^2 \exists Hc1 + k^2 \exists Ht1 - k \exists Hi1 - k^2 \exists Hc1 - k^2 \exists Ht1 = (k^2 - k) \exists Hi1$$

The harmonic processed echo signal PH is supplied to a demodulator 435a applying envelope detection. The demodulator 435a is followed by a low-pass filter 440a, which smoothes the obtained envelope of the harmonic processed echo signal PH.

The detector 420a passes this signal to a back-end processor 445. The module 445 processes the signal through further digital algorithms and other linear or non-linear signal conditioners (such as a post-beam-forming TGC and a log compressor). The signal is optionally compressed again, and then scan-converted into a video format. This process results in an image of the body part, which includes a digital representation thereof; the image is defined by a matrix (for example, with 512 rows and 512 columns) of visualizing elements, each one representing the intensity of the signal relating to a basic picture element (pixel) or volume element (voxel). The image so obtained is then passed to a monitor driver 445 for its displaying. In this way, it is possible to detect the position and the quantity of the immobilized contrast agent in the body part (as represented by the acoustic power corresponding to the intensity of the visualizing elements); this allows identifying the presence of pathologies to which the contrast agent is targeted.

Figure 4B:
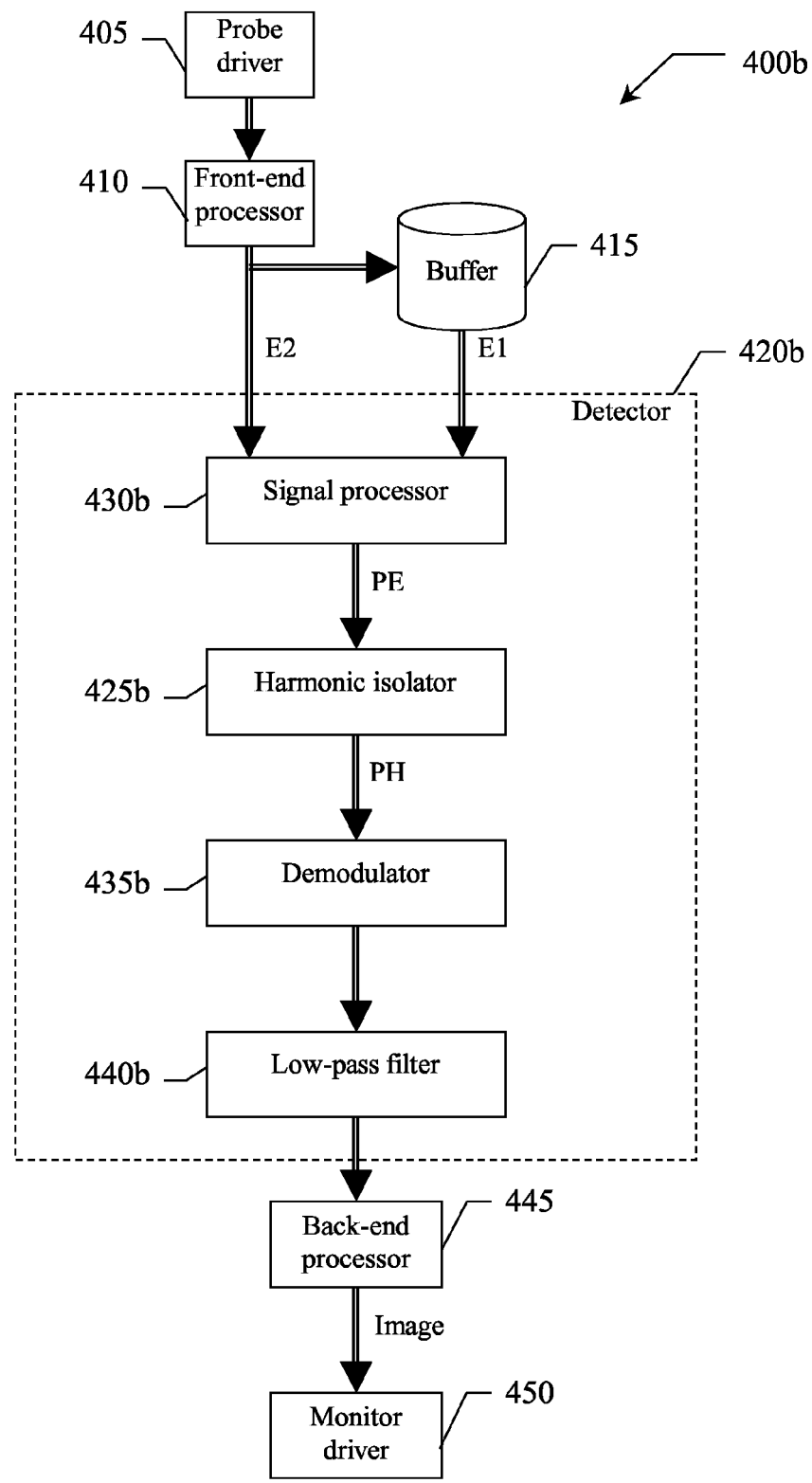

In an alternative embodiment of the invention, as shown in FIG. 4b, the corresponding main software and hardware components are denoted as a whole with the reference 400b; in the following, the elements structurally and/or functionally similar to the ones shown in the FIG. 4a will be denoted by simply changing the corresponding index (and their explanation will be omitted for the sake of brevity).

Particularly, a different detector 420b (for discriminating the contribution of the immobilized contrast agent) processes the echo signals directly and then filters them. For this purpose, the echo signal E2 (from the front-end processor 410) and to the echo signal E1 (from the buffer 415) are passed to a signal processor 430b; the signal processor 430b amplifies and subtracts the echo signals E1 and E2 so as to obtain the processed echo signal PE=$k^2 \exists$E1−E2. The processed echo signal PE is then input to a harmonic isolator 425b, which extracts the second-harmonic component of the processed echo signal PE, again equal to PH=$(k^2−k)\exists$Hi1. As in the preceding case, the harmonic processed echo signal PH is supplied to a demodulator 435b followed by a low-pass filter 440b; the resulting signal is then provided to the modules 445-450 for completing its processing.

Figure 4C:
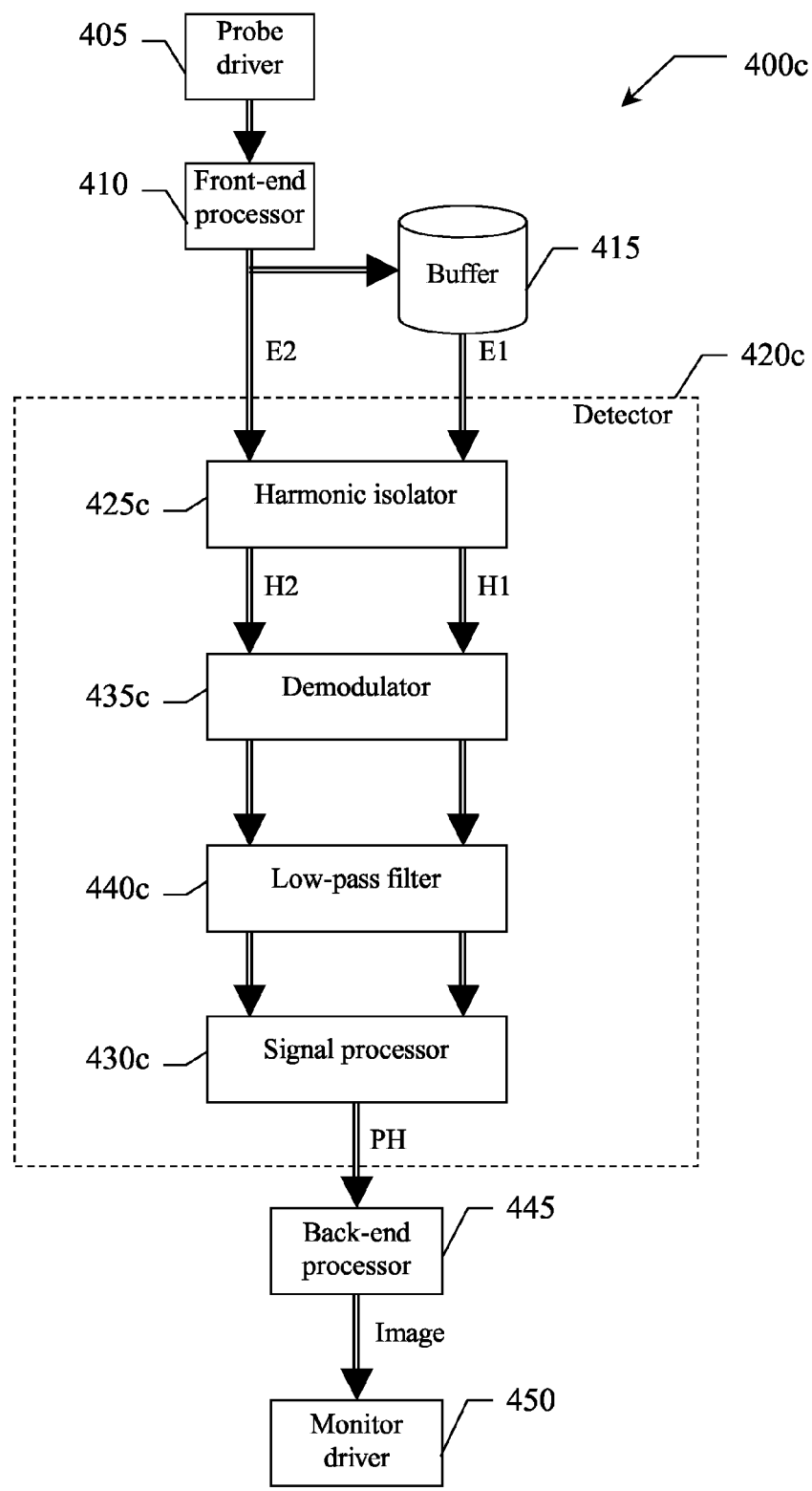

An alternative embodiment of the invention is illustrated in FIG. 4c. In this case, the corresponding main software and hardware components are denoted as a whole with the reference 400c, and include a detector 420c performing the operations in another order. More in detail, a harmonic isolator 425c (receiving the echo signals E1 and E2) now provides the harmonic echo signals H1 and H2 to a demodulator 435c followed by a low-pass filter 440c. The resulting envelopes of the harmonic echo signals H1 and H2 are passed to a signal processor 430c; the same operations described above are applied on the envelopes (instead of on the RF echo signals), thus obtaining the envelope of the harmonic processed echo signal PH. The signal obtained by the detector 420c is then passed to the modules 445-450 for completing its processing.

Figure 5A:
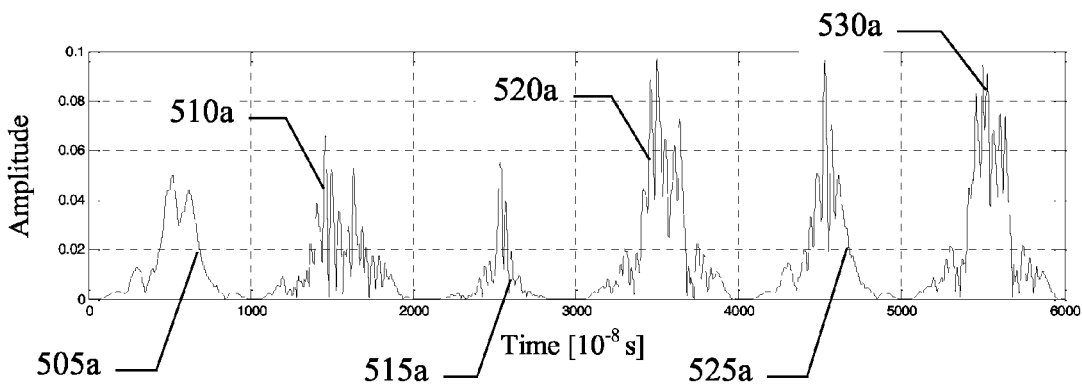
FIG. 5a traces the envelopes of experimental echo signals relating to several combinations of the immobilized contrast agent, the circulating contrast agent and the tissues.
Figure 5B:
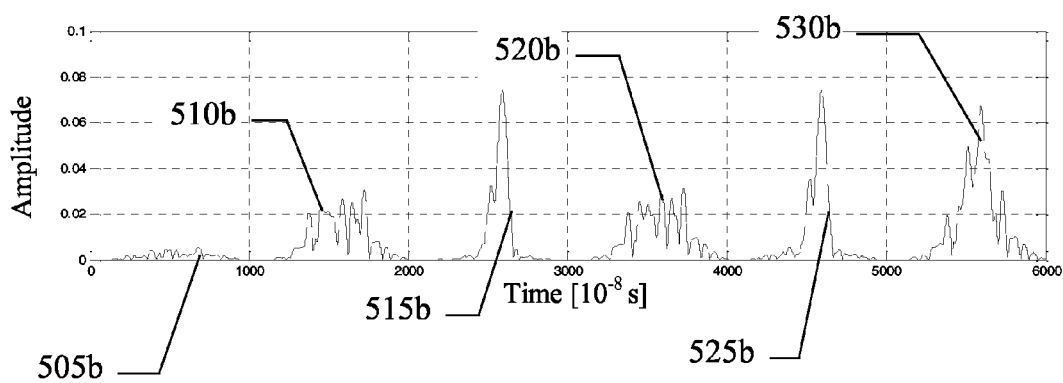
FIG. 5b traces the corresponding envelopes after the processing according to an embodiment of the invention applied on raw echo signals.
Figure 5C:
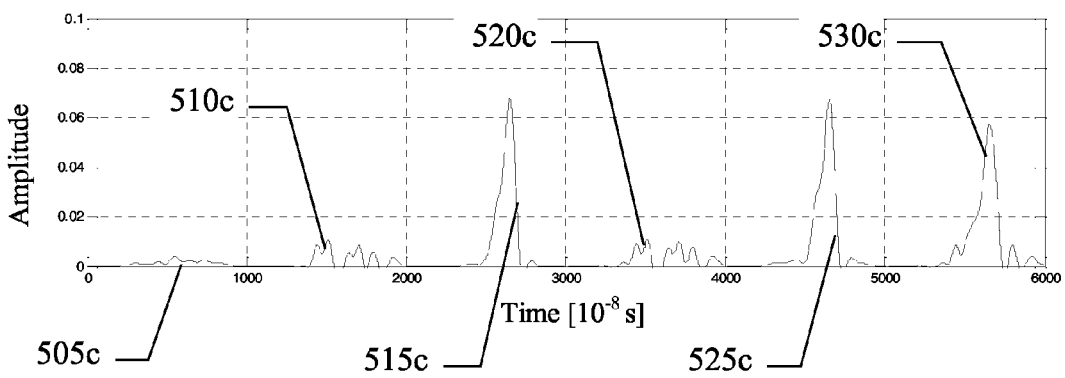
FIG. 5c traces the corresponding envelopes after the processing according to another embodiment of the invention applied on the envelopes of the echo signals.

Experimental results relating to an application of the solution according to different embodiments of the invention are illustrated in FIGS. 5a-5c. Particularly, FIG. 5a shows echo signals (recorded using a single 3 MHz pulse) from a phantom material mimicking a tissue (silicone gel with solid scatterers embedded therein), from a contrast agent in suspension (for the circulating contrast agent), and from a contrast agent held on a collagen substrate (for the immobilized contrast agent). These echo signals were grouped within segments of 1000 data points each (using a sampling rate of 100 MS/sec) with a Hanning-window apodization. The corresponding envelopes were then calculated. Particularly, the figure plots a relative amplitude of the envelope against the time for the tissue alone (portion 505a), for the circulating contrast agent alone (portion 510a), for the immobilized contrast agent alone (portion 515a), for the combination of the tissue with the circulating contrast agent (portion 520a), for the combination of the tissue with the immobilized contrast agent (portion 525a), and for the combination of the tissue, the circulating contrast agent and the immobilized contrast agent (portion 530a).

The result of the application of the above-described algorithm on the RF echo signals (implemented through the detector of FIG. 4a) is illustrated in FIG. 5b. Particularly, this figure shows the corresponding portions of the envelope (505b-530b) for the same combinations. As can be seen, the envelope for the immobilized contrast agent (portion 515b) is clearly enhanced, while the envelopes for the tissue (portion 505b) and for the circulating contrast agent (portion 510b) are reduced. As a result, it is possible to discriminate the contribution of the immobilized contrast agent when combined either with the tissue (portion 525b) or with the tissue and the circulating contrast agent (portion 530b).

The result of the application of the same algorithm on the envelopes instead of on the RF echo signals (implemented through the detector of FIG. 4c) is illustrated in FIG. 5c. Particularly, this figure shows the corresponding portions of the envelope (505c-530c) for the same combinations. In this case, the envelope for the immobilized contrast agent (portion 515c) is further enhanced, with respect to the ones for the tissue (portion 505c) and for the circulating contrast agent (portion 510c). This embodiment of the invention facilitates the discrimination of the contribution of the immobilized contrast agent when combined either with the tissue (portion 525c) or with the tissue and the circulating contrast agent (portion 530c).

According to another embodiment of the invention, it has been observed that deflated gas-filled microvesicles as well exhibit a surprising dependency law of the acoustic power of the second harmonic component of their echo signal on the acoustic pressure of the applied ultrasound waves. Indeed, it is well established that (in the fundamental frequency band) the acoustic power of the echo signal generated by gas-filled microvesicles changes linearly with the acoustic pressure of the ultrasound waves. As shown in FIG. 6a, this behavior is verified in a reproducible way for microvesicles formulated with different concentrations of $C_4F_{10}$ gas. Particularly, the figure plots the relative acoustic power (around a peak of the fundamental components of the frequency spectra) against the acoustic pressure (in logarithmic scale) for concentrations of the $C_4F_{10}$ gas in the microvesicles (reconstituted within less than one hour) equal to 35%, 10% and 5% (the remainder volume of the microvesicles being nitrogen); the resulting points are denoted with 610a, 610b and 610c, respectively. As can be seen, the corresponding dependency laws have a slope that is equal to about 20 dB/decade in all cases.

Figure 6B:
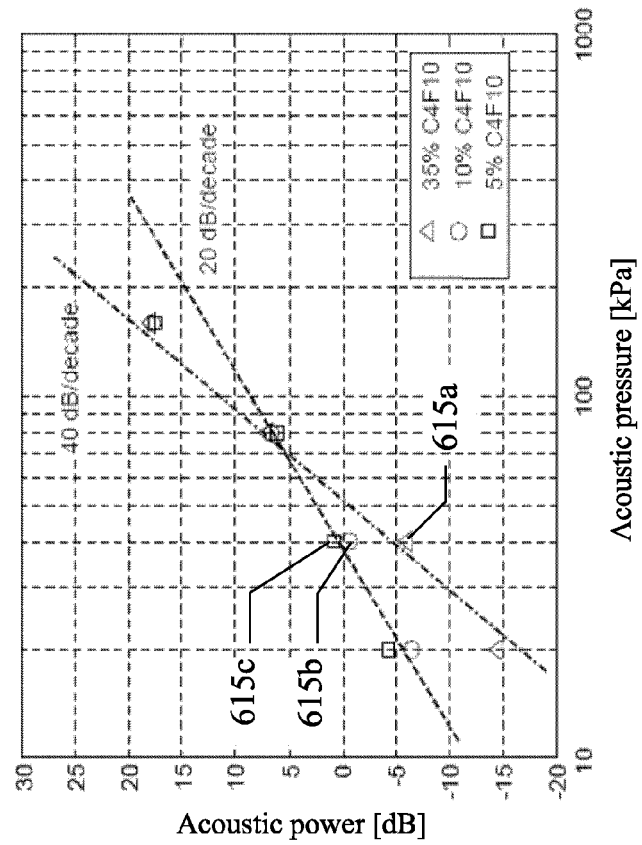
FIG. 6b shows exemplary dependency laws (of the acoustic power of the second harmonic component of the echo signals versus the acoustic pressure of the ultrasound waves) for the same microvesicles.
Figure 6A:
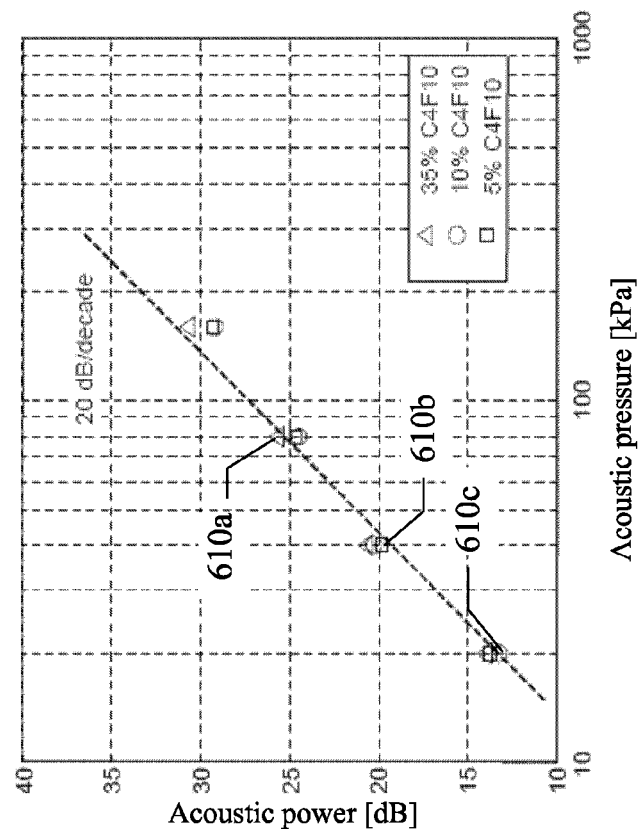
FIG. 6a shows exemplary dependency laws (of the acoustic power of the fundamental component of the echo signals versus the acoustic pressure of the ultrasound waves) for microvesicles with different gas concentrations.

Likewise, FIG. 6b plots the acoustic power of the second harmonic component of the echo signals against the acoustic pressure for the same microvesicles with $C_4F_{10}$ gas concentration of 35% (points 615a), 10% (points 615b) and 5% (points 615c). In this case, a quadratic dependency law on the acoustic pressure of the applied ultrasound waves is also expected. This behavior is verified in a reproducible way for microvesicles formulated with concentrations of $C_4F_{10}$ gas equal to 35% (or higher); indeed, the corresponding dependency law (points 615a) has a slope that is equal to about 40 dB/decade. Surprisingly, at concentrations of $C_4F_{10}$ gas equal to or lower than 10% the same dependency laws have a slope that is equal to about 20 dB/decade (points 615b and 615c); this involves a totally unexpected linear dependency law of the acoustic power of the echo signals on the acoustic pressure.

Therefore, the technique outlined above for the detection of the immobilized contrast agent may thus also be beneficial for the specific detection of this type of deflated gas-filled microvesicles against the surrounding tissues.

It should be readily apparent to those skilled in the art that the contrast agent suitable for use in the above-described method (such as including deflated gas-filled microvesicles) may be easily selected by means of conventional in-vitro methodologies (according to the teachings of the proposed solution). For example, it is possible to measure (at one or more selected harmonic, sub-harmonic or ultra-harmonic frequencies) the acoustic power of the echo signals, which are produced by a suspension of microvesicles in response to ultrasound waves with different acoustic pressures (e.g., at least two, and preferably at least four). For example, the microvesicles are placed in suspension, with suitable agitation (optionally under static or dynamic pressure conditions to simulate in-vivo conditions), and then exposed to ultrasound waves with increasing acoustic pressure (for example, in a geometric progression from 10 kPa to 1,200 kPa). For each different acoustic pressure, the resulting echo signal is recorded and its frequency power spectra is computed (e.g., by means of a Fast Fourier Transform); this allows evaluating the echo power in the various frequency bands (i.e., harmonic, sub-harmonic, ultra-harmonic bands), so as to estimate the respective dependency laws on the acoustic pressure. When the dependency law of the measured acoustic power on the applied acoustic pressure (in at least one of the considered frequency bands) differs from a quadratic dependency law as defined above the microvesicles are considered suitable for the method; for example, this happens when the dependency law has a power lower than 32 dB/decade; for example, the dependency law may have a power lower than 28 dB/decade, or lower than 24 dB/decade (such as equal to about 20 dB/decade).

EXAMPLES

The results described above with reference to FIGS. 2a-2b, 3a-3b, and 5a-5c were obtained with the following experimental procedures. First of all, two suspensions of phospholipid-stabilized gas-filled microvesicles were prepared; one suspension comprised a targeting ligand and the other one no targeting ligand, so as to provide a targeted contrast agent and a non-targeted contrast agent, respectively.

Example 1

Preparation of the Targeted Contrast Agent 200 mg of DSPC (distearoylphosphatidylcholine), 275 mg of DPPG.Na (distearoylphosphatidylglycerol sodium salt) and 25 mg of N-MPB-DPPE (1,2-dipalmitoyl-sn-glycero-3-phopshoetahnolamine-N-[4-(p-maleimidophenyl)butyramide] sodium salt, from Avanti Polar Lipids), were solubilized at 60° C. in 50 ml of hexan/isopropanol (42/8). The solvent was evaporated under vacuum, and then PEG-4000 (35.046 g) was added to the lipids and the mixture was solubilized in 106.92 g of t-butyl alcohol at 60° C., in a water bath. The solution was filled in vials with 1.5 ml of solution each. The samples were rapidly frozen at −45° C. and lyophilized. The air in the headspace was replaced with a mixture of $C_4F_{10}$/Air (50/50) and the vials were capped and crimped. The lyophilized samples were reconstituted with 10 ml of saline solution (0.9%-NaCl) per vial. RGD-4C peptide (ACDCRGDCFCG, from AnaSpec Inc., San Jose, Calif. Ref No 29897) was thyoacetilated with SATA (N-succinidimyl-S-acetylthioacetate, from Pierce) according to manufacturer's instruction. 200 μg of thioacetylated RGD-4C were dissolved in 20 μl of DMSO and then diluted in 1 ml of Phosphate Buffer Saline (PBS). This solution was mixed to the N-MPB-functionalized microbubbles dispersed in 18 ml of PBS-EDTA 10 mM, pH 7.5 and 2 ml of deacetylation solution (50 mM sodium phosphate, 25 mM EDTA, 0.5 M hydroxylamine.HCl, pH 7.5) was added. The headspace was filled with $C_4F_{10}$/Air (35/65) and the mixture was incubated for 2.5 hours at room temperature under gentle agitation (rotating wheel), in the dark. The so obtained microbubbles were washed by centrifugation.

Example 2

Preparation of the Non-Targeted Contrast Agent

DPPS (dipalmitoylphospatydilserine), in a concentration of 1.0 mg/ml (0.1%), was added to about 10 ml of an aqueous solution containing mannitol (10% w/w), heated at 65° C. for 15 minutes and then cooled at room temperature (22° C.). Perfluoroheptane (8% v/v) was added to this aqueous phase and emulsified in a beaker of about 4 cm diameter by using a high speed homogenizer (Polytron T3000, probe diameter of 3 cm) for 1 minute at a speed of 12.500 rpm. The emulsion was then centrifuged (800-1.200 rpm for 10 minutes, Sigma centrifuge $3K^{10}$) to eliminate the excess of the phospholipid and the separated pellets (microdroplets) were recovered and re-suspended in the same initial volume of a 10% mannitol aqueous solution. The washed emulsion was then collected into a 100 ml balloon for lyophilization, frozen and then freeze-dried according to the above standard procedure. The lyophilized was exposed to an atmosphere containing perfluoro-n-butane and air (50/50) and then dispersed in a volume of water twice than the initial one by gentle hand shaking.

Example 3

Execution of the Measurements

FIGS. 2a, 2b, 3a, 3b

The measurements on the immobilized contrast agent were performed by using a cell with a 5 mm thickness Rat Tail Collagen layer, Type 1 (BD Biosciences ref. 354236) cast on a 60 mm Petri dish, surrounded by a Plexiglas ring. The collagen was coated with Cell line ECV304 (a RGD-C4 binding substrate from European Collection of Animal Cell Culture, Salisbury, Wiltshire, UK, ref No. 92091712), and the targeted contrast agent of example 1 was then deposited by decantation. After incubation for 30 minutes, the cell was washed to remove unbound targeted contrast agent. For the measurements, a Vermon M3 transmitter (25.4 mm diameter, 76.2 mm focus, 2-4 MHz bandwidth, mounted at an angle of 40° with respect to the surface of the cell and at a distance of 76 mm therefrom) and a Panametrics 7.5 MHz receiver (6.35 mm diameter, unfocused, mounted at a angle of 15° with respect to the axis of the cell and at a distance of 71.3 mm therefrom) were used. The measurement parameters were: Tabor 8024, 10-cycle bursts, 3 MHz, Hanning window (for the excitation), ENI A-150 (for the amplification), Panametrics 5900, Gain 26 dB, Attenuation 0 dB (for the reception), and Backs43 "Scanning" mode, time window 10 µs, frequency 1-15 MHz (for the acquisition). The measurements were performed in two areas, each one containing 50 locations (spaced apart by 2 mm); the average of the values so obtained were then calculated.

The measurements for the non-immobilized contrast agent (prepared according to example 2) were performed with a gas volume concentration of $3 \cdot 10^6$ µm$^3$/ml. The same transmitter (at a angle of 21° with respect to the surface of the cell and at the same distance of 76 mm therefrom) and the same receiver (perpendicular to the surface of the cell and at a distance of 80.5 mm therefrom) were used; the same measurement parameters were selected (with the exception of a Gain of 40 dB for the reception).

Example 4

Execution of the Measurements

FIGS. 5a-5c

The measurements on the immobilized contrast agent were performed by using the same cell set-up and microvesicles as in example 3. The same Vermon M3 transmitter was used (at the same distance but at an angle of 45° with respect to the surface of the cell), while a Vermon M6 transducer was used as the receiver (19 mm diameter, 76.2 mm focus, 3-8 MHz bandwidth, mounted at an angle of 15° with respect to the surface of the cell and at a distance of 76 mm therefrom). The measurement parameters were: Tabor 8024, 5-cycle bursts, 3 MHz, Hanning window (for the excitation), ENI A-150 (for the amplification), Panametrics 5900, Gain 40 dB, Attenuation 0 dB (for the reception), and Backs43 "Scanning" mode, time window 10 µs, frequency 1-15 MHz (for the acquisition).

The measurements for the non-immobilized contrast agent (prepared according to example 2) were performed with a gas volume concentration of $3 \cdot 10^6$ µm$^3$/ml. The same transmitter (at a angle of 30° with respect to the surface of the cell and at the same distance of 76 mm therefrom) and the same receiver (perpendicular to the surface of the cell and at a distance of 76 mm therefrom) were used; the same measurement parameters were selected (with the exception of a gain of 40 dB for the reception). The tissue response was obtained by using a disc of tissue-mimicking phantom (ATS laboratories mod. 528) with the same transmit and receive set-ups.

MODIFICATIONS

Naturally, in order to satisfy local and specific requirements, a person skilled in the art may apply to the one or more solutions described above many modifications and alterations. Particularly, although one or more embodiments of the present invention have been described with a certain degree of particularity, it should be understood that various omissions, substitutions and changes in the form and details as well as other embodiments are possible; moreover, it is expressly intended that specific elements and/or method steps described in connection with any disclosed embodiment of the invention may be incorporated in any other embodiment as a general matter of design choice.

For example, similar considerations apply if the ultrasound scanner has a different structure or includes other units; alternatively, the filters are implemented with equivalent spectral processors (for example, based on the fast Fourier, the Chirp-Z, the short-time Fourier or the wavelet transformations).

The embodiment of the invention relating to the immobilized contrast agent may lend itself to be put into practice with equivalent contrast agents for whatever (biological) target and/or location.

Likewise, the embodiment addressing the detection of the deflated gas-filled microvesicles is not limited to the above-described contrast agents.

More generally, an embodiment of the invention may be used to discriminate a generic first type of contrast agent from a different type of contrast agent, from the surrounding tissues of from both of them.

In addition, other dependency laws on the acoustic pressure (for example, being not exactly linear and/or quadratic) may be exploited for implementing an embodiment of the present invention; moreover, an embodiment of the proposed solution can also be based on dependency laws that are different for the circulating contrast agent and for the tissues.

In any case, the application of an embodiment of the proposed solution to further harmonic, sub-harmonic or ultraharmonic components of the echo signals is not excluded.

The desired result can also be achieved by processing the echo signals with any other suitable algorithm.

Particularly, even though in the preceding description reference has been made to the combination of two echo signals, this is not to be intended as a limitation; indeed, an embodiment of the invention is also suitable to be implemented by processing three or more echo signals (thereby improving the accuracy of the results but at the cost of an increased complexity).

The principles of the invention should not be limited to the suggested values of the selected factor for combining the echo signals.

Moreover, an embodiment of the present invention lends itself to be implemented also with different values of the acoustic pressures of the ultrasound waves (even in terms relative to the destruction threshold value or in absolute terms).

Alternatively, the medical imaging system includes an ultrasound scanner and a distinct computer (or any equivalent data processing system); in this case, the measured RF echo data is transferred from the ultrasound scanner to the computer for its processing (for example, through the removable disk, a memory key, or a network connection).

Similar considerations apply if the program (which may be used to implement the invention) is structured in a different way, or if additional modules or functions are provided; likewise, the memory structures may be of other types, or may be replaced with equivalent entities (not necessarily consisting of physical storage media). Moreover, an embodiment of the proposed solution lends itself to be implemented with an equivalent method (having similar or additional steps, even in a different order). In any case, the program may take any form suitable to be used by or in connection with any data processing system, such as external or resident software, firmware, or microcode (either in object code or in source code). Moreover, the program may be provided on any computer-usable medium; the medium can be any element suitable to contain, store, communicate, propagate, or transfer the program. Examples of such medium are fixed disks (where the program can be pre-loaded), removable disks, tapes, cards, wires, fibers, wireless connections, networks, broadcast waves, and the like; for example, the medium may be of the electronic, magnetic, optical, electromagnetic, infrared, or semiconductor type.

In any case, an embodiment of the present invention lends itself to be carried out with a hardware structure (for example, integrated in a chip of semiconductor material), or with a combination of software and hardware.

The invention claimed is:

1. A medical imaging system including:
   means for receiving a plurality of echo signals indicative of a response of a body part to a plurality of ultrasound pulsed waves having different acoustic pressures, the body part including a tissue being perfused with a contrast agent, and
   means for discriminating in the echo signals a contribution of a first type of contrast agent from a contribution of a second type of contrast agent and/or of the tissue, at least one harmonic component of the contribution of the first type of contrast agent having an acoustic power changing according to a first dependency law on the acoustic pressure and the at least one harmonic component of the contribution of the second type of contrast agent and/or of the tissue having an acoustic power changing according to at least one second dependency law on the acoustic pressure, wherein the means for discriminating includes means for significantly reducing the at least one harmonic component of the contribution of the second type of contrast agent and/or of the tissue with respect to the at least one harmonic component of the contribution of the first type of contrast agent according to the corresponding dependency laws.

2. The system according to claim 1, wherein the contrast agent is capable of being immobilized on at least a part of the tissue, the first type of contrast agent being the immobilized contrast agent and the second type of contrast agent being the non-immobilized contrast agent.

3. The system according to claim 1, wherein the means for discriminating is adapted to discriminate the contribution of the first type of contrast agent from the contribution of the tissue only, the first dependency law having a power lower than 32 dB/decade.

4. The system according to claim 3, wherein the first type of contrast agent includes deflated gas-filled microvesicles.

5. The system according to claim 4, wherein the deflated gas-filled microvesicles consist of phospholipid-stabilized gas-filled microvesicles, the microvesicles having an internal volume of gas including from 0.5% to 30% by volume of a first gas having a first solubility in water below 0.0283 ml of gas per ml of water and a first molecular weight higher than 80 daltons, the remainder of said internal volume of gas being a second gas having a second solubility in water higher than the first solubility in water and/or a second molecular weight lower than the first molecular weight.

6. The system according to claim 1, wherein the first dependency law is a substantially linear dependency law, and wherein the at least one second dependency law is a substantially quadratic dependency law.

7. The system according to claim 6, wherein the substantially linear dependency law has a power from 16 dB/decade to 24 dB/decade, and wherein the substantially quadratic dependency law has a power from 32 dB/decade to 48 dB/decade.

8. The system according to claim 6, wherein the means for reducing includes means for combining the echo signals to substantially remove the at least one harmonic component of the contribution changing according to the substantially quadratic dependency law from the combined echo signals.

9. The system according to claim 8, wherein the means for reducing further includes means for filtering out a fundamental component of each echo signal and/or of the combined echo signals.

10. The system according to claim 8, wherein the echo signals consist of a first echo signal corresponding to a first ultrasound pulsed wave having a first acoustic pressure and a second echo signal corresponding to a second ultrasound pulsed wave having a second acoustic pressure, the second acoustic pressure being equal to the first acoustic pressure multiplied by a predetermined factor, and wherein the means for combining includes means for calculating a difference between the first echo signal multiplied by substantially the square of said factor and the second echo signal.

11. The system according to claim 10, wherein said factor is comprised between 1.5 and 4.

12. The system according to claim 1, wherein the at least one harmonic component is a second harmonic component.

13. The system according to claim 1, wherein the acoustic pressures are lower than a threshold value causing a destruction of substantially 10% of the contrast agent in the body part.

14. The system according to claim 13, wherein the contrast agent includes phospholipid-stabilized gas-filled microvesicles, the acoustic pressures being comprised between 20 kPa and 500 kPa.

15. The system according to claim 1, wherein the means for receiving the echo signals includes means for receiving a plurality of radio-frequency echo signals and means for determining an envelope of each radio-frequency echo signal.

16. The system according to claim 1, wherein the means for receiving the echo signals includes means for applying the ultrasound pulsed waves to the body part and means for acquiring the corresponding echo signals.

17. A medical imaging method including the steps of:
   receiving with a processor a plurality of echo signals indicative of a response of a body part to a plurality of ultrasound pulsed waves having different acoustic pressures, the body part including a tissue being perfused with a contrast agent, and
   discriminating in the echo signals, with the processor, a contribution of a first type of contrast agent from a contribution of a second type of contrast agent and/or of the tissue, at least one harmonic component of the contribution of the first type of contrast agent having an acoustic power changing according to a first dependency law on the acoustic pressure and the at least one harmonic component of the contribution of the second type of contrast agent and/or of the tissue having an acoustic power changing according to at least one second dependency law on the acoustic pressure, wherein the step of discriminating includes significantly reducing the at least one harmonic component of the contribution of the second type of contrast agent and/or of the tissue with respect to the at least one harmonic component of the contribution of the first type of contrast agent according to the corresponding dependency laws.

18. A non-transitory computer readable medium, that when executed, is operable to cause a processor to:
   receive a plurality of echo signals indicative of a response of a body part to a plurality of ultrasound pulsed waves having different acoustic pressures, the body part including a tissue being perfused with a contrast agent, and
   discriminate in the echo signals a contribution of a first type of contrast agent from a contribution of a second type of contrast agent and/or of the tissue, at least one harmonic component of the contribution of the first type of contrast agent having an acoustic power changing according to a first dependency law on the acoustic pressure and the at least one harmonic component of the contribution of the second type of contrast agent and/or of the tissue having an acoustic power changing according to at least one second dependency law on the acoustic pressure, wherein the step of discriminating includes significantly reducing the at least one harmonic component of the contribution of the second type of contrast agent and/or of the tissue with respect to the at least one harmonic component of the contribution of the first type of contrast agent according to the corresponding dependency laws.

19. A non-transitory computer program product including a computer-usable medium embodying a computer program, the computer program when executed on a data processing system causing the system to perform a medical imaging method including the steps of:
   receiving a plurality of echo signals indicative of a response of a body part to a plurality of ultrasound pulsed waves having different acoustic pressures, the body part including a tissue being perfused with a contrast agent, and
   discriminating in the echo signals a contribution of a first type of contrast agent from a contribution of a second type of contrast agent and/or of the tissue, at least one harmonic component of the contribution of the first type of contrast agent having an acoustic power changing according to a first dependency law on the acoustic pressure and the at least one harmonic component of the contribution of the second type of contrast agent and/or of the tissue having an acoustic power changing according to at least one second dependency law on the acoustic pressure, wherein the step of discriminating includes significantly reducing the at least one harmonic component of the contribution of the second type of contrast agent and/or of the tissue with respect to the at least one harmonic component of the contribution of the first type of contrast agent according to the corresponding dependency laws.

20. A method including the steps of:
   receiving with a processor a plurality of echo signals indicative of a response of a body part to a plurality of ultrasound pulsed waves having different acoustic pressures, the body part including a tissue being perfused with a contrast agent comprising microvesicles that are adapted to generate echo signals, in response to ultrasound pulsed waves, with at least one harmonic component having an acoustic power that changes according to a first dependency law on an acoustic pressure of the ultrasound pulsed waves having a power lower than 32 dB/decade, and
   discriminating in the echo signals, with a processor, a contribution of the contrast agent from a contribution of the tissue, the at least one harmonic component of the contribution of the tissue changing according to at least one second dependency law on the acoustic pressure having a power higher than 32 dB/decade, wherein the step of discriminating includes significantly reducing the at least one harmonic component of the contribution of the tissue with respect to the at least one harmonic component of the contribution of the contrast agent according to the corresponding dependency laws.

21. The method according to claim 20, wherein the first dependency law is a substantially linear dependency law, and wherein the at least one second dependency law is a substantially quadratic dependency law.

22. The method according to claim 21, wherein the substantially linear dependency law has a power from 16 dB/decade to 24 dB/decade, and wherein the substantially quadratic dependency law has a power from 32 dB/decade to 48 dB/decade.

23. A method including the steps of:
   receiving with a processor a plurality of echo signals indicative of a response of a body part to a plurality of ultrasound pulsed waves having different acoustic pressures, the body part including a tissue being perfused with a contrast agent adapted to generate echo signals, in response to ultrasound pulsed waves, with at least one harmonic component having an acoustic power that changes according to a first dependency law on an acoustic pressure of the ultrasound pulsed waves having a power lower than 32 dB/decade, and
   discriminating in the echo signals, with a processor, a contribution of the contrast agent from a contribution of the tissue, the at least one harmonic component of the contribution of the tissue changing according to at least one second dependency law on the acoustic pressure having a power higher than 32 dB/decade, wherein the step of discriminating includes significantly reducing the at least one harmonic component of the contribution of the tissue with respect to the at least one harmonic component of the contribution of the contrast agent according to the corresponding dependency laws.

* * * * *